(12) United States Patent
Dente

(10) Patent No.: US 7,183,249 B2
(45) Date of Patent: Feb. 27, 2007

(54) FRAGRANCE COMPOSITIONS AND DELIVERY SYSTEMS

(75) Inventor: Stephen V. Dente, Oakland, NJ (US)

(73) Assignee: Robertet Fragrances, Inc., Oakland, NJ (US)

( * ) Notice: Subject to any disclaimer, the term of this patent is extended or adjusted under 35 U.S.C. 154(b) by 222 days.

(21) Appl. No.: 10/171,603

(22) Filed: Jun. 14, 2002

(65) Prior Publication Data

US 2002/0198117 A1  Dec. 26, 2002

Related U.S. Application Data

(63) Continuation-in-part of application No. 09/717,412, filed on Nov. 21, 2000, now Pat. No. 6,426,325.

(51) Int. Cl.
   *C11D 3/00* (2006.01)
   *B32B 9/00* (2006.01)

(52) U.S. Cl. ............. 510/519; 510/523; 428/40.2; 239/6

(58) Field of Classification Search ........... 428/905, 428/411, 1, 40.2; 510/162, 101, 519, 523; 239/53–58, 6; 422/5, 123, 124; 134/12
   See application file for complete search history.

(56) References Cited

U.S. PATENT DOCUMENTS

| | | | |
|---|---|---|---|
| 3,567,118 A | 3/1971 | Shepherd et al. | |
| 3,655,129 A | 4/1972 | Seiner | |
| 4,226,944 A | 10/1980 | Stone et al. | |
| 4,248,380 A | 2/1981 | Lee et al. | |
| 4,567,675 A * | 2/1986 | Rennie | 34/60 |
| 4,720,417 A | 1/1988 | Sweeny et al. | |
| 4,725,575 A | 2/1988 | Frihart et al. | |
| 4,880,690 A | 11/1989 | Szycher et al. | |
| 5,102,662 A | 4/1992 | Gallagher | |
| 5,150,722 A | 9/1992 | Rutherford | |
| 5,534,229 A | 7/1996 | Nomura et al. | |
| 6,063,365 A | 5/2000 | Shefer et al. | |
| 6,089,953 A | 7/2000 | Chen | |
| 6,162,454 A | 12/2000 | Ahr et al. | |
| 6,218,013 B1 * | 4/2001 | Wood et al. | 428/411.1 |
| 6,244,265 B1 | 6/2001 | Cronk et al. | |
| 6,283,821 B1 | 9/2001 | Wang | |
| 6,293,402 B1 | 9/2001 | Rogers et al. | |
| 6,306,477 B1 | 10/2001 | Pacione | |
| 6,326,069 B1 | 12/2001 | Barnett et al. | |
| 6,364,097 B1 | 4/2002 | Whitaker et al. | |
| 6,379,689 B1 | 4/2002 | Aguadisch et al. | |
| 6,403,186 B1 | 6/2002 | Tararuj et al. | |
| 2001/0000235 A1 | 4/2001 | Bowen et al. | |
| 2001/0032801 A1 | 10/2001 | Dobler | |

FOREIGN PATENT DOCUMENTS

WO  WO 96/31244  10/1996

* cited by examiner

*Primary Examiner*—Douglas McGinty
*Assistant Examiner*—Preeti Kumar
(74) *Attorney, Agent, or Firm*—Fish & Richardson P.C.

(57) ABSTRACT

A dry fragrance composition having from about 0.1 to about 20%, by total carrier weight, of a fragrance composition substantially uniformly deposited on the surface of a non-absorbent solid inorganic particulate substrate is used to impart a fragrance to a second material. The nonabsorbent solid inorganic particulate substrate can be an alkali metal chloride, sulfates, or tripolyphosphates, soda ash, borax, or a zeolite.

14 Claims, No Drawings

FRAGRANCE COMPOSITIONS AND DELIVERY SYSTEMS

CROSS-REFERENCE TO RELATED APPLICATIONS

This is a continuation in part of applicant Ser. No. 09/717,412, filed Nov. 21, 2000 now U.S. Pat. No. 6,426,325.

FIELD OF THE INVENTION

The present invention relates to a dry fragrance composition for imparting a fragrance to a second particulate material through physical admixture.

BACKGROUND OF THE INVENTION

U.S. Pat. No. 4,020,156 to Murray discloses a fragrant bead composition with a multiplicity of prilled urea beads. The beads have an adherent surface coating consisting essentially of finely divided particles of calcium silicate, magnesium carbonate, or silicon dioxide, and dextrin as a binder. The particles have a surface area of from about 80 to about 400 square meters per gram and contain a fragrance. The adsorbent is present in a ratio of from about 1 to 5 parts per 100 parts by weight of urea and in the coating in a ratio of about 0.2 to 2 parts per part by weight of dextrin; the fragrance is present in a ratio of from 1 to 3 parts per part by weight of adsorbent.

U.S. Pat. No. 4,110,261 to Newland, discloses a molding composition of petroleum wax and a synthetic polymer with a molecular weight below 10,000 and about 15% of a fragrance. In one embodiment, this constitutes a shell about an unperfumed core of wax.

U.S. Pat. No. 4,209,417 to Whyte discloses perfumed particles having a continuous water-soluble polymer matrix in which there is uniformly dispersed perfume/emulsifier droplets. Droplets on the surface give an immediate perfume effect while droplets below the surface give a sustained release perfume. The droplets within the matrix are released upon contact with water. The perfumed particles have a particle size of from 40 microns to 1400 microns, preferably 175 microns to 1000 microns while the perfume/emulsifier droplets have diameters of from 0.01 microns to 0.5 microns.

U.S. Pat. No. 4,225,444 to Schmitt discloses butanoyl cyclohexane derivatives as a perfume which can be used in various compositions (soaps, space odorants and deodorants, colognes, toilet water, bath preparations etc.) including powders such as talcs, dusting powders, face powders and the like. The perfume composition or fragrance composition can contain a vehicle, or carrier such as a liquid such (a nontoxic alcohol or glycol such as propylene glycol) or an absorbent solid, such as gum (such as gum arabic or gelatin).

U.S. Pat. No. 4,267,166 to Yajima discloses a composition (edible particles, an edible troche, an edible liquid, chewing gum or toothpaste) for treating bad breath with from 0.5 to 50% by weight of cyclodextrin and an edible carrier for oral administration.

U.S. Pat. No. 4,904,639 to Hallam discloses an air freshener having a homogenized mixture of polyethylene glycol and water as a plasticizing agent with a perfume incorporated therein. The air freshener is made by mixing particulate solid polyethylene glycol with a plasticizing amount of water to form a slurry, heating, and agitating the slurry until it is homogenized, adding a perfume to the homogenized material while agitating to disperse the perfume, and solidifying the composition so that the perfume is dispersed throughout.

U.S. Pat. No. 5,041,421 to King discloses a fragrance having discrete pellets of compressed salt, typically sodium chloride, with a fragrant oil dispersed within the pellets. The compressed salt is disclosed as being odorless, nonflammable, nontoxic, nonallergenic, nonnutritive, environmentally safe, homogeneous, non-crumbling with a high pressure break strength, and does not melt even at elevated temperatures. The fragrance is uniformly dispersed throughout the pellets, a feature which is said to be beneficial since the composition has no surface film.

It also is generally known that particulate materials such as soaps and detergents are spray dried to remove moisture. Typically, however, the addition of a fragrance is accomplished by spraying, thereby reintroducing moisture into the spray dried material and requiring another mixing operation.

DETAILED DESCRIPTION

The dry fragrance composition of the present invention utilizes a nonabsorbent solid inorganic particulate substrate on the surface of which is substantially uniformly deposited a fragrance. The resulting fragrance composition can be used to impart a fragrance to a second particulate material, such as laundry detergents, automatic dishwasher detergents, animal litter, bath salts, carpet cleaners, rug and room deodorizers, fabric bleaches, powdered cleaners, fabric softeners, and the like, through simple physical admixture and without the need to wet or moisten the second particulate material. The fragrance and formulation of powdered, granulated, and dry blended products can thus be enhanced. The final products can be formulated as powders or in the form of unit dose, tablet, pouch, gelcap, and the like. Moreover, when the fragrance is applied to the surface of the nonabsorbent solid inorganic particulate substrate, as opposed to being dispersed in and/or throughout the second particulate material, an increase in fragrance strength and performance can be discerned, meaning that less fragrance need be added. Manufacturing is also simplified and waste is reduced since addition is more controlled and does not require spraying while at the same time the stability of the fragrance in the finished product is improved.

The nonabsorbent solid inorganic particulate substrate will be inert to the second particulate material, that is to the material to which it is to be added. Suitable nonabsorbent solid inorganic particulate substrates include alkali metal chlorides, sulfates, or tripolyphosphates, soda ash, borax, and zeolites. Preferably the nonabsorbent solid inorganic particulate substrate is sodium chloride. Combinations of nonabsorbent solid inorganic particulate substrates can be used.

Ideally the density and particle size of the nonabsorbent solid inorganic particulate substrate is selected so as to approximate the density and particle size of the second particulate material, thereby facilitating maintenance of product homogeniety. A wide variety of particle sizes for the nonabsorbent solid inorganic particulate substrates can be employed, ranging from a mesh size of from about 400 to about 10.

The amount of fragrance carried by the nonabsorbent solid inorganic particulate substrate will vary with the substrate but flowability can be readily controlled. Thus if with a given fragrance level a drier, more flowing composition is desired, a moisture absorbing material such as zeolite can be added to the nonabsorbent solid inorganic particulate substrates carrying the fragrance until the desired flowability is obtained.

The term "fragrance" as used herein refers to any odoriferous material having a vapor pressure below atmospheric pressure at ambient temperatures. The fragrance material will most often be liquid at ambient temperatures. A wide variety of chemicals are known for fragrance uses, including materials such as aldehydes, ketones, and esters. More commonly, naturally occurring plant and animal oils and exudates comprising complex mixtures of various chemical components are known for use as fragrances. The fragrances herein can be relatively simple in their composition or can comprise highly sophisticated complex mixtures of natural and synthetic chemical components, all chosen to provide any desired odor. Typical fragrances can comprise, for example, woody/earthy bases containing exotic materials such as sandalwood oil, civet and patchouli oil. The fragrances can be of a light floral fragrance, e.g. rose extract, violet extract, and lilac. The fragrances can also be formulated to provide desirable fruity odors, e.g. lime, lemon and orange. Any material which exudes a pleasant or otherwise desirable odor can be used in the present invention.

The fragrance composition is deposited on the surface of the nonabsorbent solid inorganic particulate substrate so that there is from about 0.1% to about 30%, by total carrier weight of the fragrance composition, preferably from about 1% to about 20%. Preferably there is from about 4 to about 15%, by total carrier weight of the fragrance composition. The actual fragrance component of the fragrance composition typically will be oils of organic nature having different volatilities, many of which are commercially available. Typical fragrant oils are set forth in the Kirk-Othmer Encyclopedia of Chemical Technology, 14, 2d. (1967). The particular oil selected is not critical and is a matter of choice.

The fragrance composition also can provide a visual clue, that is, it can include a coloring agent. Typically this will be a dye that is compatible with the fragrance composition. In one embodiment, the color of the fragrance composition is selected so as to contrast with the color of the second particulate material, thereby making the presence of fragrance composition visibly discernable in the second particulate material. The particular color selected, however, also is not critical and is a matter of choice.

The dry fragrance composition is prepared by mixing the selected nonabsorbent solid inorganic particulate substrate with fragrance and any coloring material. The dry fragrance composition then can be stored or shipped for subsequent mixing with a second particulate material such as a detergent.

In long term testing, the fragrance strength remains high, demonstrating both an affinity of the fragrance for the nonabsorbent solid inorganic particulate substrate and the absence of any appreciable migration to the second particulate material.

A further aspect of the invention provides for a uniform admixture of (a) a particulate material such as laundry detergents, automatic dishwasher detergents, animal litter, bath salts, carpet cleaners, rug and room deodorizers, fabric bleaches, and powdered cleaners, and (b) a quantity of a dry fragrance composition having (i) a nonabsorbent solid inorganic particulate substrate which is inert to the particulate material and consisting essentially of sodium chloride, and (ii) from about 0.1 to about 30%, by weight of the composition, of a fragrance composition substantially uniformly deposited on its surface which is sufficient to impart the fragrance to the particulate material.

Thus the present compositions are especially useful, but by no means exclusively useful, when admixed with detergent composition. Detergent compositions contain a water-soluble organic surfactant and detergency adjunct materials in addition to the dry fragrance composition. The level of surfactant depends upon the type of detergency product, but generally ranges from 0.05% to 35%. The organic surfactants can be anionic surfactants, nonionic surfactants, ampholytic surfactants, zwitterionic surfactants and mixtures thereof. The detergent composition can be a pre-soak detergent composition, main wash detergent composition, automatic dishwasher detergent, or a household cleaner detergent composition in any particulate, that is granular or powder, form. Pre-soak and household cleaner detergent compositions contain a low level of surfactant, primarily for dispersing the composition throughout the aqueous bath. A level of surfactant from 0.05% to 2%, preferably 0.25% to 1% is used. A main wash detergent composition contains from 5% to 35%, preferably 8% to 20% surfactant. The balance of the detergent composition can consist essentially of detergency adjunct materials such as a builder, soil suspending agent, processing aid, brightener, enzyme, bleach, and mixtures thereof. While the nature and amount of the adjunct materials will dependent on the use of the product, a typical detergent composition will be a built detergent composition containing from 10% to 80%, preferably 25% to 75% detergency builder. Other compositions are described by K. R. Lange in *Detergents and Cleaners*, Chapter 6, the disclosure of which is incorporated herein by reference. In each case, the dry fragrance composition described herein is admixed with these detergent compositions as herein described.

Other compositions with which the dry fragrance composition is advantageously mixed include animal litter, bath salts, carpet cleaners, rug deodorizers, room deodorizers, fabric bleaches, powdered cleaners, etc. Animal litters for example typically include a finely subdivided or powdered carrier having a powder size passing a 20 mesh standard size sieve. Such solid materials include cellulosic materials such as finely ground hay, husks, sawdust, excelsior, cereal hulls, corncobs, etc., or chlorophyll-containing-agents such as ground grasses, ground alfalfa and the like. The finely subdivided solid also can be mineral such as aluminosilicates or clay, e.g., kaolinite, halloysite, attapulgipe, montmorillonite, vermiculite, or hectorite, silica, limestone, alumina, etc. Any of the solids can be acidified with an acid to provide a neutralization capacity. A binder and water-sensitive disentegrant such as clays with water expanding crystal lattices such as bentonite and vermiculite, and water soluble or dispersible gums and polymers such as guar gum, microcrystalline cellulose and pregelatinized starches, also can be included. In each case, the dry fragrance composition described herein is admixed with these particulate materials.

The present invention also pertains to a fragrance delivery system. The fragrance delivery system comprises (i) a source of fragrance, (ii) a sealed envelope of a polymeric film completely enveloping the fragrance source, and (iii) an outer sheath of flexible material retaining the sealed envelope. The polymeric film of the sealed envelope is permeable to the fragrance but at a controlled rate that is less than the rate of release of fragrance from the fragrance source. The outer sheath of flexible material has a permeability to the fragrance exceeding that of the sealed envelope to the fragrance.

The fragrance source can consist of pure fragrance entrapped in the sealed envelope. While the undiluted fragrance might be overpowering, the polymeric film will limit its release. Alternatively, pure fragrance can be diluted with an inert solvent, the polymeric film again limiting the release of the fragrance. More preferably, the fragrance source is fragrance carried on an inert carrier, as for example deposited on the surface of salt crystals; e.g., sodium chloride; e.g., dry fragrance composition as described above.

In an alternative embodiment, the fragrance source within in the sealed envelope is latent and is activated, as by moisture, heat, etc.

Typically, the envelope of polymeric film contains no added ingredients other than those constituting the fragrance source or aiding in its function.

The polymeric film of the envelope can be any polymer inert to the fragrance source but permeable to the fragrance either inherently or as a result of processing. Suitable polymers include homopolyolefins such as polyethylene, polypropylene, mixtures thereof, and copolymers of polyolefins (with for example vinyl acetate or methyl acrylate), polyesters, polyamides, polycarbonates, regenerated cellulose, etc. The films can be mono layer or multilayer structures, as for example laminates. Films of regenerated cellulose also can be used. Heat sealable layers can be present or the film itself can be (or include) a heat sealable material. These layers are known in the art and can be formed in known manner, for example by co-extrusion or by coating.

The permeability of the film is selected to achieve the desired fragrance level of a given fragrance. The permeability of the films to the fragrance vapor usually is in the range from about 800 to about 200,000 $cm^3/m^2/day/atmosphere$. Lower permeabilities can be achieved by the use of a thicker film or by applying a coating to the film to reduce inherent permeability.

Permeability also can be modified by imperforation; i.e., introducing perforations in the film. The size of the perforations can be as low as 20 microns or less, more preferably 40 to 60 microns and, advantageously about 50 microns mean diameter. If the perforations are too large, control of the permeability may suffer. Perforations can be produced by known methods; e.g., mechanical methods, electrical discharge, lasers, etc.

Suitable materials and techniques for modifying polymeric films to alter permeability are known, see e.g., U.S. Pat. No. 5,832,699 and Japanese Patent Publication 62.148247, and do not constitute an aspect of this invention.

The outer sheath can be any flexible material such as a fabric or a nonwoven. It can be physically distinct from the polymeric film and simply form a retainer for the envelope or the outer sheath can be physically attached to the polymeric film as by lamination or by deposition.

In one particularly preferred embodiment, the envelope and outer sheath are a composite of polymeric film and nonwoven material, the polymeric film covering one face of nonwoven material and being heat sealable. The polymeric film is joined or sealed around a portion of the perimeter of the composite to a degree at least sufficient to define both the envelope (with the fragrance source such as the dry fragrance composition describe above enveloped within) and the outer sheath around the envelope.

The polymeric film of the sealed envelope not only retains the fragrance source and prevents staining, soiling, or contamination, but also because it is permeable thereto, releases fragrance vapor at a controlled rate. Moreover because the permeability rate that is less than the rate of release of fragrance from the fragrance source, the former becomes the release limiting factor. Because variations in the permeability rate of the polymeric film are less dependent on other conditions, such as temperature, and can be controlled in the course of manufacture, the release of fragrance is substantially constant and approaches zero order.

The outer sheath of flexible material serves primarily as a cover for the sealed envelope and optionally can carry graphic depictions, such as decorative patterns or pictures, business logos, advertising, etc. Because the outer sheath has a permeability to the fragrance exceeding that of the polymeric film of the sealed envelope, it does not impede the constant release provided by the film.

The following examples will serve to further typify the nature of the invention but should not be construed as a limitation on the scope thereof, which is defined solely by the appended claims.

EXAMPLE 1

| Ingredient | Amount (%) |
| --- | --- |
| Sodium Chloride (Alberger Topping Salt; mesh 20 to 40) | 93.99 |
| Coloring Solution | 0.0048 |
| Floral Fragrance (Robertet PNT57) | 4.00 |

The coloring solution is formulated from 0.333 g. of FD&C Blue #1 and 9.4 g of water. This is sprayed on the sodium chloride particles with mixing. The fragrance is then sprayed on the surface of the particles, again with mixing, and the mixture stirred until a uniform color is obtained. Zeolite can be sprinkled on the mixture to facilitate the removal of any residual moisture.

EXAMPLE 2

Four parts of the fragrance on the nonabsorbent solid inorganic particulate substrate prepared as in Example 1 are mixed with 96 parts of unscented detergent and gently mixed for 5 minutes to provide a scented detergent composition.

EXAMPLE 3

A formulation similar to that described in Example 1 is prepared utilizing 93.99% sodium chloride (pretzel salt with mesh size of 10 to 40) and replacing the zeolite with a like amount of sodium tripolyphosphate.

EXAMPLE 4

Four parts of the fragrance composition prepared in Example 3 were mixed with 96 parts of unscented detergent and the two are gently mixed for 5 minutes to provide a scented detergent composition.

EXAMPLE 5

A formulation similar to that described in Example 3 is prepared substituting however 93.99% sodium chloride (Cargill Microsized salt with a mesh size through 325) utilized in detergent compositions.

EXAMPLE 6

A total of 97.5 parts of unscented detergent and 2.5 parts of the fragrance composition prepared in Example 5 were gently mixed for 5 minutes to provide a scented detergent composition.

EXAMPLE 7

A formulation suitable for providing a fragrance to conventional cat litter is prepared utilizing 90% sodium chloride, 5% sodium tripolyphosphate, and 5% fragrance in the manner described in Example 1.

EXAMPLE 8

| Ingredient | Amount (%) |
|---|---|
| Sodium Chloride | 84 |
| Sodium Bicarbonate | 9 |
| Sodium Tripolyphosphate (Powdered) | 6 |
| Fragrance | 1 |

The sodium bicarbonate is added to the sodium chloride particles with mixing. The fragrance is sprayed on the surface of the particles and the sodium tripolyphosphate powder is then added. The mixture is stirred until it is free-flowing.

EXAMPLE 9

Sixteen parts by weight of α-olefin sulfonate are added to 1000 parts by weight of the nonabsorbent solid inorganic particulate substrate prepared as in Example 8 and the mixture stirred for five minutes to produce a scented foaming bath product.

EXAMPLE 10

| Ingredient | Amount (%) |
|---|---|
| Sodium Tripolyphosphate Hexahydrate | 50 |
| Sodium Chloride | 35.5 |
| Sodium Tripolyphosphate (Powdered) | 5 |
| White Mineral Oil | 4 |
| Water | 2.5 |
| Caprylic Capric Trigyceride | 2 |
| Fragrance | 1 |

The water is sprayed on the sodium tripolyphosphate hexahydrate with mixing which is continued for 15 minutes. The mineral oil, caprylic capric trigyceride, and fragrance are mixed and sprayed on the surface of the particles. The powdered sodium tripolyphosphate then is slowly added and the mixture stirred until it is free-flowing. The sodium chloride is added and the composition stirred for 10 minutes to produce fragranced softening bath grains

EXAMPLE 11

| Ingredient | Amount (%) |
|---|---|
| Sodium Chloride (Alberger Topping Salt; mesh 20 to 40) | 94.00 |
| Floral Fragrance (Robertet PNT57) | 6.00 |

The fragrance is sprayed on the surface of the sodium chloride particles, with mixing, and the two ingredient stirred until a uniform mixture is obtained. Zeolite can be added to facilitate the removal of any residual moisture. A 2"×4" rectangle composite of heat sealable polyethylene film and non-woven (Kimberly-Clark "KC 100 GSI Coform") is cut and a quantity of the fragrance mixture prepared above is then placed in its center of the polymeric face. The rectangle is folded over to cover the fragrance mixture and form a square which is heat sealed along the perimeter of the three (non-sealed) sides. The sealed delivery system is then inserted in a hooked, perforated container and is suitable for use as a car freshener.

What is claimed is:

1. A fragrance delivery system consisting essentially of:
   (i) a source of fragrance;
   (ii) a sealed envelope of a polymeric film completely enveloping the fragrance source, said film being permeable to the fragrance at a controlled rate less than the rate of release of fragrance from the fragrance source; and
   (iii) an outer sheath of flexible material retaining said sealed envelope and having permeability to the fragrance exceeding the permeability of the sealed envelope to the fragrance,
   whereby the fragrance is released into the ambient surroundings at the rate determined only by permeability of the polymeric film.

2. A fragrance delivery system according to claim 1 wherein the fragrance source consists of pure fragrance.

3. A fragrance delivery system according to claim 1 wherein the fragrance source is fragrance carried on a carrier.

4. A fragrance delivery system according to claim 3 wherein carrier is sodium chloride.

5. A fragrance delivery system according to claim 1 wherein the fragrance source is latent but operative when activated by moisture or heat.

6. A fragrance delivery system according to claim 1 wherein the polymeric film of the envelope comprises a polyolefin.

7. A fragrance delivery system according to claim 6 wherein the polyolefin comprises polyethylene.

8. A fragrance delivery system according to claim 6 wherein the polyolefin comprises polypropylene.

9. A fragrance delivery system according to claim 1 wherein the envelope comprises polyvinyl chloride.

10. A fragrance delivery system according to claim 1 wherein the polymeric film is perforated.

11. A fragrance delivery system according to claim 1 wherein the polymeric film is laminated to said outer sheath.

12. A fragrance delivery system according to claim 1 wherein the polymeric film is deposited on said outer sheath.

13. A fragrance delivery system according to claim 1 wherein the sheath is a nonwoven.

14. A fragrance delivery system according to claim 1 wherein the envelope and outer sheath are a composite of polymeric film covering one face of nonwoven material with said polymeric film being joined around a portion of the perimeter of the composite at least sufficient to define said envelope.

\* \* \* \* \*